US005578607A

United States Patent [19]
Cupps et al.

[11] Patent Number: 5,578,607
[45] Date of Patent: Nov. 26, 1996

[54] 6-(2-IMIDAZOLINYLAMINO)QUINOLINE COMPOUNDS USEFUL AS ALPHA-2 ADRENOCEPTOR AGONISTS

[75] Inventors: Thomas L. Cupps, Oxford; Peter J. Maurer, Cincinnati; Jeffrey J. Ares, Hamilton, all of Ohio

[73] Assignee: The Procter & Gamble Company, Cincinnati, Ohio

[21] Appl. No.: 326,564

[22] Filed: Oct. 20, 1994

Related U.S. Application Data

[63] Continuation-in-part of Ser. No. 169,343, Dec. 17, 1993, abandoned.

[51] Int. Cl.$^6$ .......................... C07D 403/12; A61H 31/47
[52] U.S. Cl. .................................. 514/314; 546/171
[58] Field of Search ............................ 546/171; 514/314

[56] References Cited

U.S. PATENT DOCUMENTS

| | | | |
|---|---|---|---|
| 3,890,319 | 6/1975 | Danielewicz et al. | 260/250 |
| 4,029,792 | 6/1977 | Danielewicz et al. | 424/251 |
| 4,036,976 | 7/1977 | Neumann | 424/273 |
| 4,217,356 | 8/1980 | Neumann | 424/270 |
| 4,398,028 | 8/1983 | Neumann | 544/331 |
| 5,021,416 | 6/1991 | Gluchowski | 514/249 |
| 5,091,528 | 2/1992 | Gluchowski | 544/105 |
| 5,180,721 | 1/1993 | Burke | 514/213 |
| 5,231,096 | 7/1993 | Gluchowski et al. | 514/249 |
| 5,281,591 | 1/1994 | Burke | 514/213 |

FOREIGN PATENT DOCUMENTS

| | | | |
|---|---|---|---|
| 0047328 | 3/1982 | European Pat. Off. | C07D 403/12 |
| 0025269 | 3/1991 | European Pat. Off. | A61K 31/155 |
| 2638356 | 4/1990 | France | A61K 31/415 |

OTHER PUBLICATIONS

Cambridge, D., "UK–14,304, A Potent and Selective $\alpha_2$–Agonist for the Characterization of $\alpha$–Adrenoceptor Subtype", *European Journal of Pharmacology*, vol. 72, pp. 413–415 (1981).

Chapleo, C. B., J. C. Doxey, P. L. Myers, M. Myers, C. F. C. Smith and M. R. Stillings "Effect of 1,4–Dioxanyl Substitution on the Adrenergic Activity of some Standard $\alpha$–Adrenoreceptor Agents", *European Journal of Medicinal Chemistry*, vol. 24, pp. 619–622 (1989).

Chapleo, C. B., R. C. M. Butler, D. C. England, P. L. Myers, A. G. Roach, C. F. C. Smith, M. R. Stillings and I. F. Tulloch, "Heteroaromatic Analogues of the $\alpha_2$–Adrenoreceptor Partial Agonist Clondine", *J. Med. Chem.*, vol. 32, pp. 1627–1630 (1989).

Clare, K. A., M. C. Scrutton and N. T. Thompson, "Effects of $\alpha_2$–Adrenoreceptor Agonists and of Related Compounds on Aggregation of, and on Adenylate Cyclose Activity in, Human Platelets", *Br. J. Pharmacl*, vol. 82, pp. 467–476 (1984).

Timmermans, P. B. M. W. M. and P. A. van Zwieten, "$\alpha_2$–Adrenoceptor Agonists and Antagonists", *Drugs of the Future*, vol., 9, No. 1, pp. 41–55 (Jan., 1984).

Timmermans, P. B. M. W. M. A. T. Chiu and M. J. M. C. Thoolen, "12,1$\alpha_2$–Adrenergic Receptors", *Comprehensive Medicinal Chemistry*, vol. 3, Membranes & Receptors, pp. 133–185 (1990).

Timmermans, P. B. M. W. M. A. de Jonge, M. J. M. C. Thoolen, B. Wilffert, H. Batink and P. A. van Zwieten, "Quantitative Relationships between $\alpha_2$–Adrenergic Activity and Binding Affinity of $\alpha_2$–Adrenoceptor Agonists and Antagonists", *J. Med. Chem.*, vol. 27, pp. 495–503 (1984).

Megens, A. A. H. P., J. E. Leysen, F. H. L. Awouters and C. J. E. Niemegeers, "Ruther Validation of In Vivo and In Vitro Pharmacological Procedures for Assessing the $\alpha_2/\alpha_1$–Selectivity of Test Compounds: (2) $\alpha$–Adrenoceptor Agonists", *European Journal of Pharmacology*, vol. 129, pp. 57–64 (1986).

Van Meel, J. C. A., A. de Jonge, P. B. M. W. M. Timmermans and P. A. van Zwieten, "Selectivity of Some Alpha Adrenoceptor Agonists for Peripheral Alpha–1 and Alpha–2 Adrenoceptors in the Normotensive Rat", *The Journal of Pharmacology and Experimental Therapeutics*, vol. 219, pp. 760–767 (1981).

Zinchenko, T. M., "Investigation of Autollergenic Action of Dibutyl and Dioctyl Phthalates", *Gig. Sanit.*, vol. 1, pp. 79–80.

*Primary Examiner*—David B. Springer
*Attorney, Agent, or Firm*—Karen F. Clark; Richard A. Hake; Mary Pat McMahon

[57] ABSTRACT

The subject invention relates to compounds having the structure:

wherein:
(a) R is unsubstituted $C_1$–$C_3$ alkanyl or alkenyl;
(b) R' is selected from unsubstituted $C_1$–$C_3$ alkanyl or alkenyl; unsubstituted $C_1$–$C_3$ alkylthio or alkoxy; hydroxy; thiol; and halo; and
(c) R" is selected from hydrogen; unsubstituted $C_1$–$C_3$ alkanyl or alkenyl; methyl monosubstituted with hydroxy, thiol or amino; unsubstituted $C_1$–$C_3$ alkylthio or alkoxy; amino; unsubstituted amide; unsubstituted or $C_1$–$C_3$ substituted amido; halo; unsubstituted sulfoxide; unsubstituted sulfonyl; and cyano;

pharmaceutical compositions containing such compounds, and the use of such compounds for preventing or treating respiratory, ocular, and/or gastrointestinal disorders.

17 Claims, No Drawings

6-(2-IMIDAZOLINYLAMINO)QUINOLINE COMPOUNDS USEFUL AS ALPHA-2 ADRENOCEPTOR AGONISTS

This is a continuation-in-part of application Ser. No. 08/169,343, filed on Dec. 17, 1993, abandoned.

TECHNICAL FIELD

The subject invention relates to certain substituted 6-(2-imidazolinylamino)quinoline compounds. The compounds have been found to be selective alpha-2 adrenoceptor agonists and are useful for treatment of one or more of respiratory disorders, particularly nasal congestion; ocular disorders, particularly glaucoma; and gastrointestinal disorders, particularly diarrhea.

BACKGROUND OF THE INVENTION

Information regarding alpha adrenergic receptors, agonists and antagonists, in general, and regarding compounds related in structure to those of the subject invention are disclosed in the following references: Timmermans, P. B. M. W. M., A. T. Chiu & M. J. M. C. Thoolen, "12.1 α-Adrenergic Receptors", *Comprehensive Medicinal Chemistry*, Vol. 3, Membranes & Receptors, P. G. Sammes & J. B. Taylor, eds., Pergamon Press (1990), pp. 133–185; Timmermans, P. B. M. W. M. & P. A. van Zwieten, "α-Adrenoceptor Agonists and Antagonists", *Drugs of the Future*, Vol. 9, No. 1, (January, 1984), pp. 41–55; Megens, A. A. H. P., J. E. Leysen, F. H. L. Awouters & C. J. E. Niemegeers, "Further Validation of in vivo and in vitro Pharmacological Procedures for Assessing the $\alpha_1$ and $\alpha_2$-Selectivity of Test Compounds: (2) α-Adrenoceptor Agonists", *European Journal of Pharmacology*, Vol. 129 (1986), pp. 57–64; Timmermans, P. B. M. W. M., A. de Jonge, M. J. M. C. Thoolen, B. Wilffert, H. Batink & P. A. van Zwieten, "Quantitative Relationships between α-Adrenergic Activity and Binding Affinity of α-Adrenoceptor Agonists and Antagonists", *Journal of Medicinal Chemistry*, Vol. 27 (1984) pp. 495–503; van Meel, J. C. A., A. de Jonge, P. B. M. W. M. Timmermans & P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics*, Vol. 219, No. 3 (1981), pp. 760–767; Chapleo, C. B., J. C. Doxey, P. L. Myers, M. Myers, C. F. C. Smith & M. R. Stillings, "Effect of 1,4-Dioxanyl Substitution on the Adrenergic Activity of Some Standard α-Adrenoreceptor Agents", *European Journal of Medicinal Chemistry*, Vol. 24 (1989), pp. 619–622; Chapleo, C. B., R. C. M. Butler, D. C. England, P. L. Myers, A. G. Roach, C. F. C. Smith, M. R. Stillings & I. F. Tulloch, "Heteroaromatic Analogues of the $\alpha_2$-Adrenoreceptor Partial Agonist Clondine", *J. Med. Chem.*, Vol. 32 (1989), pp. 1627–1630; Clare, K. A., M. C. Scrutton & N. T. Thompson, "Effects of $\alpha_2$-Adrenoceptor Agonists and of Related Compounds on Aggregation of, and on Adenylate Cyclase Activity in, Human Platelets", *Br. J. Pharmac.*, Vol. 82 (1984), pp. 467–476; U.S. Pat. No. 3,890,319 issued to Danielewicz, Snarey & Thomas on Jun. 17, 1975; and U.S. Pat. No. 5,091,528 issued to Gluchowski on Feb. 25, 1992. However, many compounds related in structure to those of the subject invention do not provide the activity and specificity desirable when treating respiratory, ocular or gastrointestinal disorders.

It is particularly relevant to the subject invention that compounds found to be effective nasal decongestants are frequently found to have undesirable side effects, such as causing hypertension and insomnia. There is a need for new drugs which provide relief from nasal congestion without causing these undesirable side effects.

It is an object of the subject invention to provide novel compounds having substantial activity in preventing or treating nasal congestion.

It is a further object of the subject invention to provide such compounds which do not cause hypotension, drowsiness, hypertension, insomnia or other undesirable side effects.

It is also an object of the subject invention to provide novel compounds for treating cough, chronic obstructive pulmonary disease (COPD) and/or asthma.

It is also an object of the subject invention to provide novel compounds for treating glaucoma and/or diarrhea.

It is a still further object of the subject invention to provide such compounds which have good activity from peroral and/or topical dosing.

SUMMARY OF THE INVENTION

The subject invention relates to compounds having the structure:

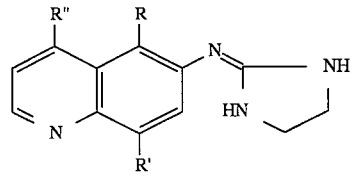

wherein:

(a) R is unsubstituted $C_1$–$C_3$ alkanyl or alkenyl;

(b) R' is selected from unsubstituted $C_1$–$C_3$ alkanyl or alkenyl; unsubstituted $C_1$–$C_3$ alkylthio or alkoxy; hydroxy; thiol; and halo; and (c) R" is selected from hydrogen; unsubstituted $C_1$–$C_3$ alkanyl or alkenyl; methyl monosubstituted with hydroxy, thiol or amino; unsubstituted $C_1$–$C_3$ alkylthio or alkoxy; amino; unsubstituted amide; unsubstituted or $C_1$–$C_3$ substituted amido; halo; unsubstituted sulfoxide; unsubstituted sulfonyl; and cyano;

pharmaceutical compositions containing such compounds, and the use of such compounds for preventing or treating respiratory, ocular, and/or gastrointestinal disorders.

DETAILED DESCRIPTION OF THE INVENTION

As used herein, "alkyl" means a straight or branched hydrocarbon chain, saturated or unsaturated, unsubstituted or substituted. Unless otherwise specified, preferred alkyl is alkanyl or alkenyl as defined herein, especially alkanyl; preferred alkyl is $C_1$–$C_3$, particularly $C_2$, and especially methyl; and preferred alkyl is unsubstituted.

As used herein, "alkanyl" means a saturated hydrocarbon substituent, straight or branched chain, unsubstituted or substituted.

As used herein, "alkenyl" means a hydrocarbon substituent with one double bond, straight or branched chain, unsubstituted or substituted.

As used herein, "alkylthio" means a substituent having the structure Q—S—, where Q is alkyl.

As used herein, "alkoxy" means a substituent having the structure Q—O—, where Q is alkyl.

As used herein, "amide" means a substituent having the structure NH₂—CO—, where one or both hydrogens on the nitrogen can be substituted with alkyl.

As used herein, "amido" means a substituent having the structure H—CO—NH—, where the hydrogen, on the carbon can be substituted with alkyl.

As used herein, "halo" means fluoro, chloro, bromo and iodo.

As used herein, "sulfoxide" means a substituent having the structure HSO—, where the hydrogen can be substituted with alkyl.

As used herein, "sulfonyl" means a substituent having the structure HSO₂—, where the hydrogen can be substituted with alkyl.

COMPOUNDS

The subject invention involves novel compounds having the following structure:

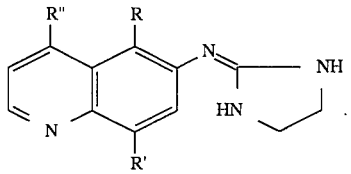

In the above structure, R is unsubstituted alkanyl or alkenyl having from 1 to about 3 carbon atoms. R is preferably alkanyl. R is more preferably methyl or ethyl, most preferably methyl.

In the above structure, R' is selected from unsubstituted alkanyl or alkenyl having from 1 to about 3 carbon atoms; unsubstituted alkylthio or alkoxy having from 1 to about 3 carbon atoms; hydroxy; thiol; and halo. R' is preferably alkanyl, more preferably methyl or ethyl, most preferably methyl. R' which is alkylthio or alkoxy is preferably saturated, also preferably C₁ or C₂, more preferably methylthio or methoxy. R' which is halo is preferably chloro or bromo, more preferably chloro.

In the above structure, R" is selected from hydrogen; unsubstituted alkanyl or alkenyl having from 1 to about 3 carbon atoms; methyl monosubstituted with hydroxy, thiol or amino; unsubstituted alkylthio or alkoxy having from 1 to about 3 carbon atoms; amino; halo; unsubstituted amide; amido, unsubstituted or substituted with alkanyl or alkenyl having from 1 to about 3 carbon atoms; unsubstituted sulfoxide; unsubstituted sulfonyl; and cyano. R" which is alkanyl or alkenyl is preferably unsubstituted. R" is also preferably alkanyl, more preferably methyl or ethyl, most preferably methyl. R" which is alkylthio or alkoxy is preferably saturated, also preferably C₁ or (C₂, more preferably methylthio or methoxy. R" which is halo is preferably fluoro, chloro or bromo, more preferably chloro, or especially fluoro. R" which is amido is preferably unsubstituted or substituted with methyl or ethyl. R" is also preferably cyano.

Preferred compounds of the subject invention are compounds having the following structure:

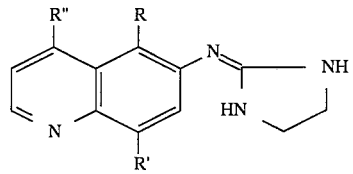

where R, R' and R" are as indicated in the following table:

| Compound No. | R | R' | R" |
| --- | --- | --- | --- |
| 1 | CH₃ | Cl | H |
| 2 | CH₃ | CH₃ | H |
| 3 | CH₃ | CH₃ | CH₃ |
| 4 | CH₃ | CH₃ | OCH₃ |
| 5 | CH₃ | OCH₃ | H |
| 6 | CH₃ | CH₃ | Cl |
| 7 | CH₃ | CH₃ | F |
| 8 | CH₃ | CH₃ | CN |

The compounds of the subject invention are particularly useful for the treatment of nasal congestion associated with allergies, colds, and other nasal disorders with associated nasal congestion, as well as their sequelae (for example, sinusitis and otitis). At the same time, it has been found that undesired side effects, such as hypotension, drowsiness, hypertension, or insomnia can be avoided. While not limited to a particular mechanism of action, the subject compounds are believed to provide advantages in the treatment of nasal decongestion over related compounds through their ability to interact with alpha-2 adrenoceptors. The subject compounds have been found to be alpha-2 adrenoceptor agonists which cause constriction of peripheral vascular beds in the turbinates. The subject compounds have been found to have only weak alpha-1 agonist activity, and have little or no effect on the central nervous system.

The compounds of the subject invention are also useful for the treatment of ocular disorders associated with increased intraocular pressure, such as glaucoma. The compounds are administered either perorally, or topically as drops, gels or creams directly to the surface of the mammalian eye.

The compounds of the subject invention are also useful for controlling gastrointestinal motility disorders, such as diarrhea, by antimotility and antisecretory actions on the gastrointestinal tract.

The pharmacological activity and selectivity of the subject compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., *The Alpha-2 Adrenergic Receptors*, L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *J. Neural. Trans.*, Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", *Arch. Otolarynng*, Vol. 96 (1972), pp. 524–529). Antiglaucoma activity is determined by measuring intraocular pressure. (See, e.g., Potter, D., "Adrenergic Pharmacology of Aqueous Human Dynamics", *Pharmacol. Rev.*, Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-Induced Diarrhea by Alpha-2 Adrenoceptor Agonists", *Aliment. Pharmacol. Therap.*, Vol. 5 (1991), pp. 255–262). Antiasthma activity is determined by measuring the effect of the compound on bronchoconstriction associated with pulmonary challenges such as inhaled antigens. (See, e.g., Chang, J. J. Musser & J. Hind, "Effects of a Novel Leukotriene $D_4$ Antagonist with 5-Lipoxygenase and Cyclooxygenase Inhibitory Activity, Wy-45,911, on Leukotriene-$D_4$- and Antigen-Induced Bronchoconstriction in Guinea Pig", *Int. Arch. Allergy Appl. Immun.*, Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *Am. Rev. Respir. Dis.*, Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled Alpha-2-Adrenoceptor and $GABA_B$ Receptor Agonists on Citric Acid-Induced Cough and Tidal Volume Changes in Guinea Pigs", *Eur. J. Pharmacol.*, Vol. 220 (1992), pp. 187–195).

The compounds of the subject invention are synthesized using the following general procedures:

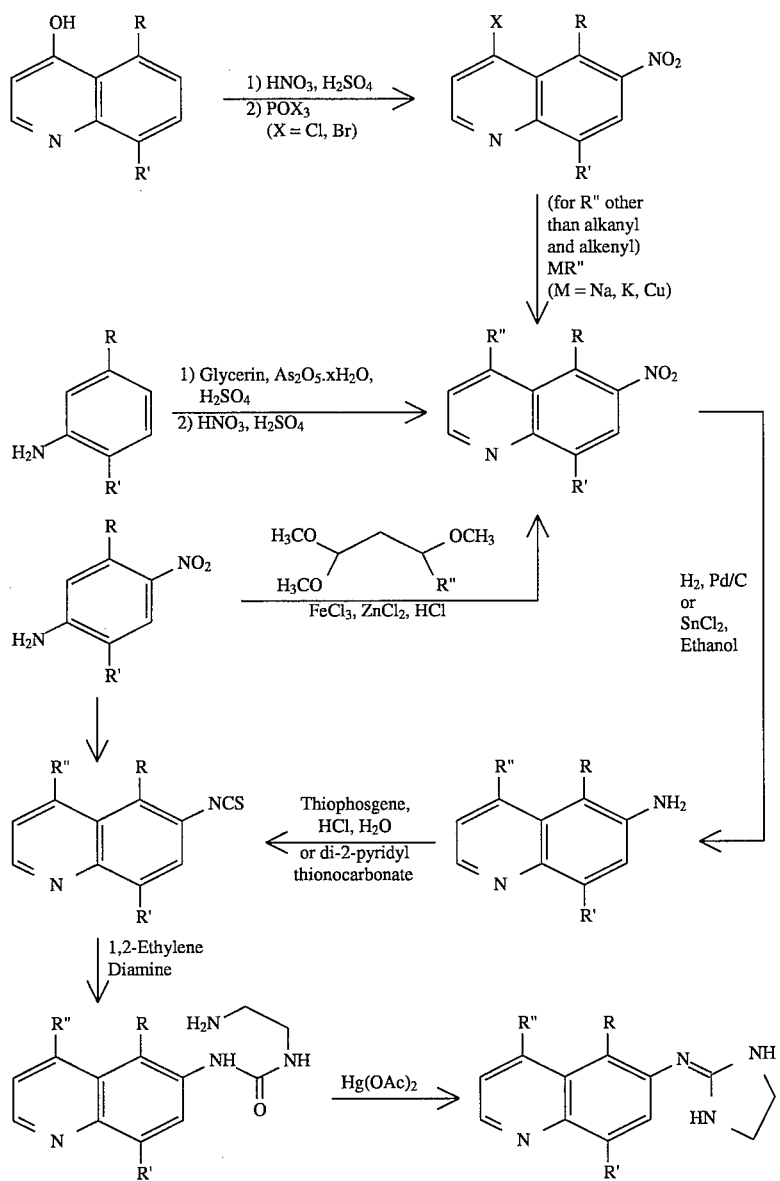

In the above scheme, where R' is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281). In the above scheme, when R"=cyano, the cyano moiety can be converted to substituted methyl or amide by standard functional group conversions. (See March, *Advanced Organic Chemistry*, 3rd ed., Wiley, 1985).

The following non-limiting examples provide details for the syntheses of compounds of 6-(2-imidazolinylamino)quinoline the subject invention.

EXAMPLE 1

Synthesis of
5,8-dimethyl-6-(2-imidazolinylamino)quinoline

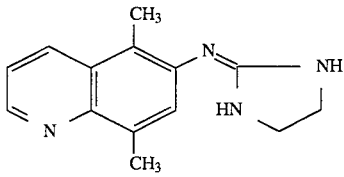

5,8-Dimethylquinoline.

To a mixture of 2,5-dimethylaniline (20.73 g), glycerin (54.81 g) and arsenic pentoxide hydrate ($As_2O_5 \cdot xH_2O$) (Aldrich, 54% As, 35.06 g) under argon and in a 1 L 3-neck round bottom flask equipped with a mechanical stirrer is carefully added sulfuric acid (51.6 g). The resulting hot solution is then heated at 140°–150° C. for 4 hours. The reaction mixture is then cooled to room temperature and slowly basified to pH=10 by the addition of ammonium hydroxide solution (28–30%). After a period of about 10 minutes the basic solution is acidified to pH=5 by the addition of glacial acetic acid and extracted with methylene chloride ($CH_2Cl_2$) (3×500 mL). The organic layer is then washed with water (2×500 mL) and brine (2×500 mL), dried over magnesium sulfate ($MgSO_4$), filtered, and rotary evaporated to yield crude quinoline (31 g) which is flash chromatographed on silica gel eluting with 10% ethyl acetate/hexane. Compound-containing fractions are combined and rotary evaporated to yield 5,8-dimethylquinoline.

5,8-Dimethyl-6-nitroquinoline.

5,8-dimethylquinoline (1.25 g), in a 250 mL round bottom flask is cooled to 0° C. in an ice-NaCl bath under argon. Concentrated sulfuric acid (50 mL) is added slowly via addition funnel so that the internal temperature does not exceed 5° C. The solution is allowed to stir a few minutes then cooled to −15° C. in an ethylene glycol-dry ice bath. Nitric acid (1.7 mL, 69–71%) in sulfuric acid (50 mL) is added dropwise (via syringe) at such a rate that the reaction temperature does not exceed −3° C. After 10 minutes, the reaction is poured into a beaker of ice and basified slowly to pH 10 by the addition of ammonium hydroxide solution (28–30%). The product is extracted with ethyl acetate (3×500 mL). The organic layer is dried over $MgSO_4$, filtered, and rotary evaporated to yield crude product (2.6 g) which is flash chromatographed on silica gel eluting with 15% ethyl acetate/hexane. Compound-containing fractions are combined and rotary evaporated to yield 5,8-dimethyl-6-nitroquinoline.

5,8-Dimethyl-6-aminoquinoline.

To a solution of 5,8-dimethyl-6nitroquinoline (1.41 mL) in ethanol (17.4 mL) under argon is added iron (Fe) (1.21 g) and glacial acetic acid (2.56 g). The mixture is refluxed for two hours. More Fe (1.23 g) and glacial acetic acid (2.49 g) are added to the reaction, which is allowed to reflux for an additional hour. The reaction is poured into a beaker of ice and adjusted to pH 10 by careful addition of a saturated solution of potassium carbonate. The product is extracted with methylene chloride and the organic layer is dried over sodium sulfate, filtered, and rotary evaporated to give 5,8-dimethyl-6-aminoquinoline.

5,8-Dimethyl-6-isothiocyanotoquinoline.

To a solution of 5,8-dimethyl-6-aminoquinoline (0.85 g) in 0.1N HCl (52 mL) is added thiophosgene (0.4 mL) dropwise. The reaction is stirred for 10 minutes, by which time a yellow precipitate has formed. 1N sodium hydroxide (NaOH) (52 mL) is added to the reaction and a white precipitate forms immediately. The reaction mixture is allowed to stir 10 minutes, after which time the product is extracted with methylene chloride (3×100 mL). The organic layer is evaporated to a small volume and the residue filtered through a bed of silica gel, which is eluted with 25% ethyl acetate/hexane. The filtrate is evaporated to yield 5,8-dimethyl-6-isothiocyantoquinoline.

6-(N-2-aminoethyl)thioureido-5,8-dimethylquinoline.

To a solution of ethylene diamine (2.00 mL) in toluene (21 mL) under argon is added dropwise a solution of 5,8-dimethyl-6-isothiocyanatoquinoline (0.88 g) in toluene (21 mL). A white precipitate forms during the addition. The toluene is evaporated and the yellow-white solid dried under a vacuum for 20 minutes to yield 6-(N-2-aminoethyl)thio-ureido-5,8-dimethylquinoline.

5,8-Dimethyl-6-(2-imidazolinylamino)quinoline dihydrochloride.

A mixture of 6-(N-2-aminoethyl)thioureido-5,8-dimethylquinoline (1.12 g) and mercuric acetate (1.85 g) in ethanol (41 mL) is heated to reflux. As the reaction warms to reflux, the mixture turns dark brown. After a few minutes at reflux temperature, the reaction becomes black. The cooled reaction mixture is filtered through a bed of celite, which is washed with ethanol. The filtrate is rotary evaporated and the residue taken up in water and basified to pH 10 with a saturated solution of potassium carbonate. The product is extracted with chloroform (3×250 mL). The organic layer is evaporated to a small volume which is then filtered through a bed of silica gel to remove residual mercury salts. The bed is washed with copious amounts of methanol and the filtrate is rotary evaporated to yield 1.3 g of crude product. A solution (10 mL) of this crude material in methylene chloride is filtered through another bed of silica gel to remove baseline material, washing the bed with 20% sat. methanolic $NH_3$/chloroform and rotary evaporated to a crude material which is suspended in boiling ethyl acetate and filtered hot. The filtered material is the desired 5,8-dimethyl-6-(2-imidazolinylamino)quinoline (0.51 g). A dihydrochloride salt is generated by bubbling HCl through a cold suspension of the quinoline in methanol. The methanol is rotary evaporated to a residue which recrystallizes from ethanol/ether to yield 5,8-dimethyl-6-(2-imidazolinylamino)quinoline dihydrochloride.

EXAMPLE 2

Synthesis of
6-(2-imidazolinylamino)-4,5,8-trimethylquinoline

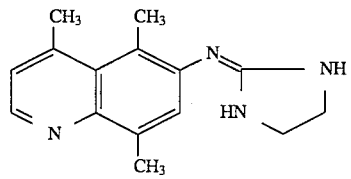

6-Nitro-4,5,8-trimethylquinoline.

A mixture of 2,5-dimethyl-4-nitroaniline (0.96 g), ferric chloride hexahydrate (2.50 g), zinc chloride (0.094 g), concentrated hydrochloric acid (0.481 mL), and ethanol (8 mL) is heated to 60° C. 1,3,3-trimethoxybutane (0.73 mL) is added dropwise while the reaction mixture is kept at 60° C. The reaction mixture is heated at reflux overnight and cooled to room temperature. A solution of 10% aqueous sodium hydroxide is added, and the mixture is extracted three times with methylene chloride. The combined organic layers are dried over sodium sulfate, filtered and evaporated to afford a crude product. The crude product is purified by flash chromatography using 25% ethyl acetate in hexane as eluent, providing 6-nitro-4,5,8-trimethylquinoline.

6-Amino-4,5,8-trimethylquinoline.

A mixture of 6-nitro-4,5,8-trimethylquinoline (0.60 g), tin(II)chloride dihydrate (3.13 g), and ethanol (40 mL) is heated for 3 hours at 60°–65° C. and then cooled to room temperature. 10% Aqueous sodium hydroxide (24 mL) and water (48 mL) are added, and the mixture is extracted three times with chloroform. The combined organic layers are washed with saturated sodium bicarbonate solution, dried over sodium sulfate, filtered and evaporated to afford a crude product. The crude product is purified by flash chromatography using 25% ethyl acetate in hexane as eluent, providing 6-amino-4,5,8-trimethylquinoline.

6-Isothiocyanato-4,5,8-trimethylquinoline.

A mixture of 6-amino-4,5,8trimethylquinoline (0.37 g), di-2-pyridyl thionocarbonate (0.494 g) (DPT) (Aldrich), dimethylaminopyridine (0.052 g) and methylene chloride (4 mL) is stirred at room temperature for 2 hours. An additional 100 mg of DPT is added, and stirring is continued for one hour. Another 100 mg portion of DPT is added, and the reaction is stirred at room temperature for one more hour. The mixture is concentrated by evaporation and purified by chromatography through a short column consisting of layers of sand/flash silica gel/sand, using 20% ethyl acetate in hexane as the eluting solvent, providing 6-isothiocyanato-4,5,8-trimethylquinoline.

N-(2-Aminoethyl)-N'-(6-(4,5,8-trimethylquinolinyl)thiourea.

To a solution of ethylene diamine (0.586 mL) in 2.5 mL of toluene is slowly added a solution of 6-isothiocyanato-4,5,8-trimethylquinoline (0.40 g) in toluene (10 mL). The reaction mixture is stirred at room temperature for 2 hours and then placed in a refrigerator overnight. The solid which forms is filtered, washed well with toluene, and dried, providing N-(2-aminoethyl)-N'-(6-(4,5,8-trimethylquinolinyl))thiourea.

6-(2-Imidazolinylamino)-4,5,8-trimethylquinoline.

A mixture of N-(2-aminoethyl)-N'-(6-(4,5,8-trimethylquinolinyl))thiourea (0.461 g), mercuric (II) acetate (0.602 g), and methanol (20 mL) is stirred at room temperature for 4 hours. The reaction mixture is filtered through Celite, and the Celite is washed well with methanol. The filtrate is evaporated. The crude product is purified by flash chromatography, eluting with a 20% methanol in methylene chloride solution, containing 1% ammonium hydroxide, providing 6-(2-imidazolinylamino)-4,5,8-trimethylquinoline.

6-(2-Imidazolinylamino)-4,5,8-trimethylquinoline dihydrochloride monohydrate.

6-(2-Imidazolinylamino)-4,5,8-trimethylquinoline (0.406 g) is dissolved in a solution of concentrated hydrochloric acid (0.813 mL) in methanol (4 mL). To this solution is added ether (7 mL). The solution is allowed to stand at room temperature for 3 days, and the resulting crystals are filtered and washed with ether to provide 6-(2-imidazolinylamino)-4,5,8-trimethylquinoline dihydrochloride monohydrate.

EXAMPLE 3

Synthesis of 5,8-dimethyl-6-(2-imidazolinylamino)-4-methoxyquinoline

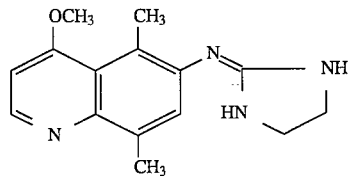

5,8-Dimethyl-6-nitro-4-quinolone.

In a flask is placed 5,8-dimethyl-4-quinolone (5.18 g, 29.9 mmol) (prepared according to Burckhalter, et al., *J. Am. Chem. Soc.*, Vol. 70 (1948), p. 1363) with sulfuric acid (30 mL). After stirring for 10 minutes, the flask is cooled in ice and concentrated nitric acid (1.90 mL, 30.2 mmol) is added dropwise. After the addition is completed, the mixture is stirred for 15 minutes in ice. The mixture is then poured onto crushed ice and allowed to warm to room temperature. The gray solid is filtered and washed with water. The solid is recrystallized from hot methanol to give 5,8-dimethyl-6-nitro-4-quinolone.

4-Chloro-5,8-dimethyl-6-nitroquinoline.

In a flask is placed 5,8-dimethyl-6-nitro-4-quinolone (3.01 g, 13.8 mmol) with phosphorus oxychloride (41.3 g, 268 mmol). The mixture is refluxed under argon with stirring for 3 hours. After cooling to room temperature the mixture is poured on crushed ice, and concentrated ammonium hydroxide (100mL) is added. Extraction with chloroform (2×200 mL), drying over potassium carbonate, filtration and solvent removal by rotary evaporation gives 4-chloro-5,8-dimethyl-6-nitroquinoline.

5,8-Dimethyl-4-methoxy-6-nitroquinoline. In a flask is placed 4-chloro-5,8-dimethyl-6-nitroquinoline (1.52 g, 5.4 mmol) with sodium methoxide (2.27 g, 4.2 mmol) and methanol (25 mL). The mixture is refluxed under argon with stirring for 21 hours, diluted with water (100 mL) and methanol (50 mL) and extracted with dichloromethane (2×200 mL). The organic layer is dried over potassium carbonate, filtered and evaporated. The product is purified by flash chromatography (7/3 hexanes/ethyl acetate), yielding 5,8-dimethyl-4-methoxy-6-nitroquinoline.

4-Amino-5,8-dimethyl-4-methoxyquinoline.

In a flask is placed 5,8-dimethyl-4-methoxy-6-nitroquinoline (1.16 g, 5.0 mmol) with stannous chloride dihydrate (5.64 g, 25 mmol) and ethanol (50 mL). The mixture is refluxed for 1 hour, diluted with water (100 mL) and concentrated ammonium hydroxide (30 mL), and extracted with chloroform (2×200 mL). The organic portion is dried over potassium carbonate, filtered and the solvents removed by rotary evaporation, yielding 4-amino-5,8-dimethyl-4-methoxyquinoline.

5,8-Dimethyl-6-isothiocyanato-4-methoxyquinoline.

A solution of 6-amino-5,8-dimethyl-4-methoxyquinoline (987 mg, 4.9 mmol), di-2-pyridylthionocarbonate (1.74 g, 7.5 mmol), and dichloromethane (70 mL) is stirred at room temperature for 2 hours. The solvent is removed by rotary evaporation and the product is purified by flash chromatography (8/2 hexanes/ethyl acetate) to give 5,8-dimethyl-6-isothiocyanato-4-methoxyquinoline.

5,8-Dimethyl-4-methoxy-6-(-N-(2-aminoethyl)thioureido)quinoline.

To ethylene diamine (2.25 g, 37 mmol) is added dropwise a solution of 5,8-dimethyl-6-isothiocyanato-4-methoxyquinoline (501 mg, 2.1 mmol) dissolved in dichloromethane (20 mL). The mixture is stirred at room temperature overnight. The resulting solid is removed by filtration and washed with a small volume of dichloromethane. The remaining solid is dried under a vacuum for several hours, providing 5,8-dimethyl-4-methoxy-6-(-N-(2-aminoethyl)thioureido)quinoline.

5,8-Dimethyl-4-methoxy-6-(2-imidazolinylamino)quinoline.

A mixture of 5,8-dimethyl-4-methoxy-6-(-N-(2-aminoethyl)thioureido)quinoline (493 mg, 1.6 mmol) and mercuric acetate (537 mg, 1.7 mmol) in methanol (60 mL), is stirred at room temperature for 2 hours, and then filtered through Celite. The filtrate is added to 10% aqueous potassium carbonate (100 mL), extracted with chloroform (3×200 mL). The organic layer is dried over potassium carbonate, filtered and evaporated to a residue which is purified by flash chromatography (9/1 chloroform/methanol saturated with ammonia) providing 5,8-dimethyl-4-methoxy-6-(2-imidazolinylamino)quinoline. This compound is converted to its dihydrochloride hemihydrate salt with 12N HCl in methanol/ether.

EXAMPLE 4

Synthesis of 4-cyano-5,8-dimethyl-6-(2-imidazolinylamino)quinoline

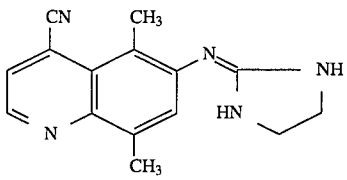

4-Bromo-5,8-dimethyl-6-nitroquinoline.

A mixture of 5,8-dimethyl-6-nitro-4-quinolone (7.12 g, 32.7 mmol), phosphorus oxybromide (7.47 g, 26.12 mmol), pyridine (5.3 mL), and toluene (90 mL) is heated at 90° C. for 6 hours. The mixture is filtered hot, and the solid is washed with water and methylene chloride. The filtrate is extracted with methylene chloride (3×100 mL), and the combined organic layers are dried (sodium sulfate) and evaporated to afford 4-bromo-5,8-dimethyl-6-nitroquinoline.

4-Cyano-5,8-dimethyl-6-nitroquinoline.

A mixture of 4-bromo-5,8-dimethyl-6-nitroquinoline (3.87 g, 13.77 mmol), cuprous cyanide (3.67 g, 41.31 mmol) and dimethylformamide (70 mL) is stirred at room temperature for 30 minutes and then heated to 155° C. and stirred at this temperature for 1 hour. Water is added, and the reaction mixture is filtered. The precipitate is washed with water and methylene chloride. The filtrate is extracted with methylene chloride (3×125 mL), and the combined organic layers are dried (sodium sulfate) and evaporated. Purification by chromatography through a short column consisting of layers of sand/flash silica gel/sand, using chloroform as eluent, provides 4-cyano-5,8-dimethyl-6-nitroquinoline.

6-Amino-4-cyano-5,8-dimethylquinoline.

A mixture of 4-cyano-5,8-dimethyl-6-nitroquinoline (2.54 g, 11.2 mmol), stannous chloride dihydrate (12.6 g, 55.9 mmol) and ethanol (200 mL) is heated at 60° C. for 1.5 hours. The reaction is cooled to room temperature, and water (60 mL) is added. The mixture is basified with 10% aqueous sodium hydroxide solution (70 mL) and subsequently extracted with methylene chloride (3×150 mL). Drying (sodium sulfate) and evaporation provides 6-amino-4-cyano-5,8-dimethylquinoline.

4-Cyano-5,8-dimethyl-6-isothiocyanatoquinoline.

A mixture of 6-amino-4-cyano-5,8-dimethylquinoline (2.0 g, 10.15 mmol), di-2-pyridyl thionocarbonate (2.52 g, 10.86 mmol), dimethylaminopyridine (0.266 g, 2.18 mmol) and methylene chloride (62 mL) is stirred at room temperature for 1.5 hours. Evaporation affords a residue which is purified by chromatography through a short column consisting of layers of sand/flash silica gel/sand, using methylene chloride as eluent, to give 4-cyano-5,8-dimethyl-6-isothiocyanatoquinoline.

6-(N-2-Aminoethyl)thiouriedo-4-cyano-5,8-dimethylquinoline.

To a solution of ethylenediamine (2.93 mL) in toluene (30 mL) is slowly added a solution of 4-cyano-5,8-dimethyl-6-isothiocyanatoquinoline (2.1 g, 8.78 mmol) in toluene (100 mL). The reaction mixture is stirred at room temperature overnight. The solid which forms is filtered, washed well with toluene, and dried to afford 6-(N-2-aminoethyl)thiouriedo-4-cyano-5,8-dimethylquinoline.

4-Cyano-5,8-dimethyl-6-(2-imidazolinylamino)quinoline.

A mixture of 6-(N-2-aminoethyl)thiouriedo-4-cyano-5,8-dimethylquinoline (2.49 g, 8.32 mmol), mercuric acetate (2.81 g, 8.82 mmol) and methanol (100 mL) is stirred at room temperature for 2 hours, resulting in a black suspension. The suspension is filtered through a bed of silica gel and celite, and the bed is washed well with methanol. The filtrate is evaporated to dryness. Purification is accomplished by chromatography through a short column consisting of layers of sand/flash silica gel/sand, using methylene chloride/methanol/ammonium hydroxide (85/15/2) as eluent. This provides 4-cyano-5,8-dimethyl-6-(2-imidazolinylamino)quinoline (partially as acetate salt).

COMPOSITIONS

Another aspect of the subject invention is compositions which comprise a safe and effective amount of a subject compound, or a pharmaceutically-acceptable salt thereof, and a pharmaceutically-acceptable carrier. As used herein, "safe and effective amount" means an amount of the subject compound sufficient to significantly induce a positive modification in the condition to be treated, but low enough to avoid serious side effects (at a reasonable benefit/risk ratio), within the scope of sound medical judgement. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.0001% to about 99% by weight of the subject compound, more preferably from about 0.01% to about 90%; also preferably from about 10% to about 50%, also preferably from about 5% to about 10%, also preferably from about 1% to about 5%, and also preferably from about 0.1% to about 1%.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

The preferred mode of administering the subject compounds is perorally. The preferred unit dosage form is therefore tablets, capsules, lozenges, chewable tablets, and the like. Such unit dosage forms comprise a safe and effective amount of the subject compound, which is preferably from about 0.01 mg to about 200 mg, more preferably from about 0.1 mg to about 50 mg, more preferably still from about 0.5 mg to about 25 mg, also preferably from about 1 mg to about 10 mg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD & C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A preferred mode of administering the subject compounds is topically to the site where activity is desired: intranasal doses for nasal decongestion, inhalants for asthma, eye drops, gels and creams for ocular disorders, and peroral doses for gastrointestinal disorders.

Preferred compositions of the subject invention include aqueous solutions comprising a safe and effective amount of a subject compound intended for topical intranasal administration. Such compositions preferably comprise from about 0.001% to about 5% of a subject compound, more preferably from about 0.01% to about 0.5%. Such compositions also typically include safe and effective amounts of preservatives, such as benzalkonium chloride and thimerosal; buffers such as phosphate and acetate; tonicity agents such as sodium chloride; antioxidants such as ascorbic acid; aromatic agents; and acids and bases to adjust the pH of these aqueous compositions as needed.

Preferred compositions of the subject invention include aqueous solutions, suspensions, and dry powders comprising a safe and effective amount of a subject compound intended for atomization and topical inhalation administration. Such compositions preferably comprise from about 0.1% to about 50% of a subject compound, more preferably from about 1% to about 20%. Such compositions are typically contained in a container with attached atomizing means. Such compositions also typically include propellants such as chlorofluorocarbons 12/11 and 12/114; solvents such as water, glycerol and ethanol; stabilizers such as ascorbic acid, sodium metabisulfite; preservatives such as cetylpyridinium chloride and benzalkonium chloride; tonicity adjustors such as sodium chloride; and flavoring agents such as sodium saccharin.

Preferred compositions of the subject invention include aqueous solutions comprising a safe and effective amount of a subject compound intended for topical intraocular administration. Such compositions preferably comprise from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Preferred compositions of the subject invention include solids, such as tablets and capsules, and liquids, such as solutions, suspensions and emulsions (preferably in soft gelatin capsules), comprising a safe and effective amount of a subject compound intended for topical administration to the gastrointestinal tract by peroral administration. Such compositions preferably comprise from about 0.01 mg to about 100 mg per dose, more preferably from about 0.1 mg to about 5 mg per dose. Such compositions can be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Compositions of the subject invention may optionally include other drug actives. Non-limiting examples of drug actives which may be incorporated in the subject compositions, and typical dosage amounts of them, include: respiratory drug actives: classical antihistamines, e.g., chlorpheniramine from about 1 mg to about 4 mg per dose, and diphenhydramine from about 10 mg to about 50 mg per dose; nonsedating antihistamines, e.g., terfenadine from about 30 mg to about 60 mg per dose, loratadine from about 5 mg per dose to about 10 mg per dose, and cetirizine from about 5 mg per dose to about 10 mg per dose; expectorants, e.g., guaifenesin from about 100 mg to about 200 mg per dose; antitussives, e.g., dextromethorphan from about 5 mg to about 30 mg per dose; and analgesics, e.g., ibuprofen from about 100 mg to about 800 mg per dose, and acetaminophen from about 80 mg to about 1000 mg per dose; ocular drug actives: acetylcholinesterase inhibitors, e.g., echothiophate from about 0.03% to about 0.25% in topical solution; and gastrointestinal actives: antidiarrheals, e.g., loperamide from about 0.1 mg to about 1.0 mg per dose, and bismuth subsalicylate from about 25 mg to about 300 mg per dose.

METHODS

Another aspect of the subject invention involves methods for preventing or treating nasal congestion by administering a safe and effective amount of a subject compound to a human or lower animal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to the subject invention is preferably from about once to about six times daily, more preferably from about 2 times to about 4 times daily. Such doses and frequencies are also preferred for treating other respiratory conditions, such as otitis media, cough, COPD and asthma.

Another aspect of the subject invention involves methods for preventing or treating glaucoma by administering a safe and effective amount of a subject compound to a human or lower animal experiencing or at risk of experiencing glaucoma. Each administration of a dose of the subject compound preferably administers a dose within the range of from about 0.01 µg/kg to about 10 mg/kg of a compound, more preferably from about 0.001 mg/kg to about 1 mg/kg, more preferably still from about 0.01 mg/kg to about 0.1 mg/kg. Intraocular administration of such doses is preferred. The frequency of administration of a subject compound according to the subject invention is preferably from about once to about six times daily, more preferably from about 2 times to about 4 times daily.

Another aspect of the subject invention involves methods for preventing or treating functional bowel disorders, such as diarrhea, by administering a safe and effective amount of a subject compound to a human or lower animal experiencing or at risk of experiencing diarrhea. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to the subject invention is preferably from about once to about six times daily, more preferably from about 2 times to about 4 times daily.

The following non-limiting examples illustrate the compositions and methods of use of the subject invention.

EXAMPLE 4

Oral Tablet Composition

| Ingredient | Amount per tablet (mg) |
| --- | --- |
| Subject Compound 2 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 |

One tablet is swallowed by a patient with nasal congestion. The congestion is substantially diminished.

EXAMPLE 5

Chewable Tablet Composition

| Ingredient | Amount per tablet (mg) |
| --- | --- |
| Subject Compound 1 | 15.0 |
| Mannitol | 255.6 |
| Microcrystalline cellulose (Avicel PH 101 ®) | 100.8 |
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 |

One tablet is chewed and swallowed by a patient with nasal congestion. The congestion is substantially reduced.

EXAMPLE 6

Sublingual Tablet Composition

| Ingredient | Amount per tablet (mg) |
| --- | --- |
| Subject Compound 7 | 2.00 |
| Mannitol | 2.00 |
| Microcrystalline cellulose (Avicel PH 101 ®) | 29.00 |
| Miny flavorants | 0.25 |
| Sodium saccharin | 0.08 |
| Total = | 33.33 |

One tablet is placed under the tongue of a patient with nasal congestion and allowed to dissolve. The congestion is rapidly and substantially diminished.

EXAMPLE 7

Intranasal Solution Composition

| Ingredient | Composition (% w/v) |
| --- | --- |
| Subject Compound 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

EXAMPLE 8

Intranasal Gel Composition

| Ingredient | Composition (% w/v) |
| --- | --- |
| Subject Compound 4 | 0.10 |
| Benzalkonium chloride | 0.02 |
| Thimerosal | 0.002 |
| Hydroxypropyl methylcellulose (Metolose 65SH4000 ®) | 1.00 |
| Aromatics | 0.06 |
| Sodium chloride (0.65%) | q.s. |
| Total = | 100.00 |

One-fifth of a mL of the composition is applied as drops from a dropper into each nostril of a patient with nasal congestion. The congestion is substantially reduced.

EXAMPLE 9

Inhalation Aerosol Composition

| Ingredient | Composition (% w/v) |
| --- | --- |
| Subject Compound 6 | 0.5 |
| Alcohol | 33.0 |
| Ascorbic acid | 0.1 |
| Menthol | 0.1 |
| Sodium Saccharin | 0.2 |
| Propellant(F12, F114) | q.s. |
| Total = | 100.0 |

Two-puffs of the aerosol composition is inhaled from a metered-dose inhaler by a patient with asthma. The asthmatic condition is effectively relieved.

EXAMPLE 10

Topical Ophthalmic Composition

| Ingredient | Composition (% w/v) |
| --- | --- |
| Subject Compound 1 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.00 |

One-tenth of a mL of the composition is administered directly into each eye of a patient with glaucoma. The intraocular pressure is substantially reduced.

EXAMPLE 11

Oral Liquid Composition

| Ingredient | Amount/15 mL Dose |
| --- | --- |
| Subject Compound 5 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 7.65 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | q.s. |
| Total = | 15 mL |

One 15 mL dose of the liquid composition is swallowed by a patient with nasal congestion and runny nose due to allergic rhinitis. The congestion and runny nose are effectively reduced.

EXAMPLE 12

Oral Liquid Composition

| Ingredient | Amount/15 mL Dose |
| --- | --- |
| Subject Compound 8 | 30 mg |
| Sucrose | 8.16 g |

-continued

| Ingredient | Amount/15 mL Dose |
|---|---|
| Glycerin | 300 mg |
| Sorbitol | 300 mg |
| Methylparaben | 19.5 mg |
| Propylparaben | 4.5 mg |
| Menthol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified Water | q.s. |
| Total = | 15 mL |

One 15 mL dose of the alcohol-free liquid medication is swallowed by a patient with nasal congestion. The congestion is substantially diminished.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having the following structure:

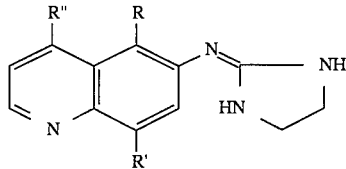

wherein:

(a) R is unsubstituted alkanyl or alkenyl having from 1 to about 3 carbon atoms;

(b) R' is selected from the group consisting of unsubstituted alkanyl or alkenyl having from 1 to about 3 carbon atoms; unsubstituted alkylthio or alkoxy having from 1 to about 3 carbon atoms; hydroxy; thiol; and halo; and (c) R" is selected from the group consisting of hydrogen; unsubstituted alkanyl or alkenyl having from 1 to about 3 carbon atoms; methyl monosubstituted with hydroxy, thiol or amino; unsubstituted alkylthio or alkoxy having from 1 to about 3 carbon atoms; amino; unsubstituted amide; amido, unsubstituted or substituted with alkanyl or alkenyl having from 1 to about 3 carbon atoms; halo; unsubstituted sulfoxide; unsubstituted sulfonyl; and cyano.

2. The compound of claim 1 wherein R" is selected from the group consisting of hydrogen, unsubstituted alkanyl or alkenyl having from 1 to about 3 carbon atoms, unsubstituted alkylthio or alkoxy having from 1 to about 3 carbon atoms; cyano; amino; and halo.

3. The compound of claim 2 wherein R is methyl and any alkyl portion of R' is methyl.

4. The compound of claim 2 wherein R is alkanyl, and R' is selected from the group consisting of methyl, ethyl, methoxy, chloro and bromo.

5. The compound of claim 1 wherein any alkyl portion of R" is unsubstituted.

6. The compound of claim 4 wherein R" is selected from the group consisting of hydrogen, methyl, ethyl, methoxy, cyano, chloro and fluoro.

7. The compound of claim 3 wherein R is methyl.

8. The compound of claim 6 wherein R is methyl.

9. The compound of claim 5 wherein both R and R' are methyl.

10. The compound of claim 3 wherein R is methyl or ethyl, and R" is hydrogen.

11. The compound of claim 8 wherein R" is selected from the group consisting of hydrogen, cyano and fluoro.

12. The compound of claim 9 wherein R" is hydrogen.

13. A pharmaceutical composition comprising:

(a) a safe and effective amount of a compound of any of claims 1, 5 or 8, and (b) a pharmaceutically-acceptable carrier.

14. A method for preventing or treating nasal congestion by administering perorally, to a human or lower animal in need of such treatment, a safe and effective amount of a compound of any of claims 1, 6 or 12.

15. A method for preventing or treating glaucoma by administering, to a human or lower animal in need of such treatment, a safe and effective amount of a compound of claims 1 or 8.

16. A method for preventing or treating diarrhea by administering perorally, to a human or lower animal in need of such treatment, a safe and effective amount of a compound of claims 1 or 8.

17. A method for preventing or treating asthma by administering perorally, to a human or lower animal in need of such treatment, a safe and effective amount of a compound of any one of claims 1 or 8.

* * * * *